United States Patent
Wang et al.

(10) Patent No.: US 9,504,590 B2
(45) Date of Patent: *Nov. 29, 2016

(54) STENT RETAINED ON A BALLOON CATHETER

(71) Applicant: Abbott Cardiovascular Systems Inc., Santa Clara, CA (US)

(72) Inventors: Yunbing Wang, Sunnyvale, CA (US); Gregory Kilinski, San Jose, CA (US); Luis Vazquez, Lathrop, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 197 days.

This patent is subject to a terminal disclaimer.

(21) Appl. No.: 14/059,382

(22) Filed: Oct. 21, 2013

(65) Prior Publication Data

US 2014/0052235 A1 Feb. 20, 2014

Related U.S. Application Data

(60) Division of application No. 13/252,965, filed on Oct. 4, 2011, now Pat. No. 8,739,384, which is a continuation of application No. 11/864,834, filed on Sep. 28, 2007, now Pat. No. 8,046,897.

(51) Int. Cl.
  *A61F 2/958* (2013.01)
  *B23P 11/00* (2006.01)
  *A61F 2/95* (2013.01)

(52) U.S. Cl.
  CPC ........ *A61F 2/958* (2013.01); *A61F 2002/9522* (2013.01); *B23P 11/005* (2013.01); *Y10T 29/49865* (2015.01); *Y10T 29/49908* (2015.01); *Y10T 29/49911* (2015.01); *Y10T 29/49913* (2015.01); *Y10T 29/49925* (2015.01); *Y10T 29/49934* (2015.01)

(58) Field of Classification Search
  CPC ..... B23P 11/005; B23P 11/02; B23P 11/025; A61F 2002/95; A61F 2002/958; A61F 2002/9522; A61F 2002/9583; A61M 25/1018; A61M 2025/1018; Y10T 29/49863; Y10T 29/49906; Y10T 29/49908; Y10T 29/49911; Y10T 29/49913
  USPC .................. 604/500, 96.01, 103.06, 103.07, 604/103.08, 103.09; 623/1.11, 1.12, 1.23
  See application file for complete search history.

(56) References Cited

U.S. PATENT DOCUMENTS

| 4,733,665 A | 3/1988 | Palmaz |
| 4,800,882 A | 1/1989 | Gianturco |

(Continued)

FOREIGN PATENT DOCUMENTS

| EP | 1 295 570 | 3/2003 |
| JP | 2004-527285 | 9/2004 |

(Continued)

OTHER PUBLICATIONS

U.S. Appl. No. 11/330,927, filed Jan. 11, 2006, Wu et al.

(Continued)

*Primary Examiner* — Christopher Besler
(74) *Attorney, Agent, or Firm* — Squire Patton Boggs (US) LLP

(57) ABSTRACT

A balloon is inflated from a collapsed configuration, then deflated. A polymeric stem is then disposed over the deflated balloon and the stent crimped to the balloon.

17 Claims, 3 Drawing Sheets

(56) References Cited

U.S. PATENT DOCUMENTS

| | | |
|---|---|---|
| 4,886,062 A | 12/1989 | Wiktor |
| 5,507,768 A | 4/1996 | Lau et al. |
| 5,514,154 A | 5/1996 | Lau et al. |
| 5,556,383 A | 9/1996 | Wang et al. |
| 5,569,295 A | 10/1996 | Lam |
| 5,836,965 A | 11/1998 | Jendersee et al. |
| 5,913,871 A | 6/1999 | Werneth et al. |
| 5,976,181 A | 11/1999 | Whelan et al. |
| 6,488,688 B2 | 12/2002 | Lim et al. |
| 6,629,350 B2 | 10/2003 | Motsenbocker |
| 6,745,445 B2 | 6/2004 | Spilka |
| 6,863,683 B2 | 3/2005 | Schwager et al. |
| 7,010,850 B2 | 3/2006 | Hijikema et al. |
| 7,316,148 B2 | 1/2008 | Asmus et al. |
| 7,761,968 B2 | 7/2010 | Huang et al. |
| 7,951,185 B1 | 5/2011 | Abbate et al. |
| 8,046,897 B2 | 11/2011 | Wang et al. |
| 8,123,793 B2 | 2/2012 | Roach et al. |
| 2002/0143382 A1 | 10/2002 | Hijlkema et al. |
| 2004/0078953 A1 | 4/2004 | Spilka |
| 2004/0106973 A1 | 6/2004 | Johnson |
| 2005/0119720 A1 | 6/2005 | Gale et al. |
| 2005/0143752 A1 | 6/2005 | Schwager et al. |
| 2005/0244533 A1 | 11/2005 | Motsenbocker et al. |
| 2006/0047336 A1 | 3/2006 | Gale et al. |
| 2007/0271763 A1 | 11/2007 | Huang et al. |
| 2007/0282433 A1 | 12/2007 | Limon et al. |
| 2007/0289117 A1 | 12/2007 | Huang et al. |
| 2008/0016668 A1 | 1/2008 | Huang et al. |
| 2008/0033523 A1 | 2/2008 | Gale et al. |
| 2008/0033524 A1 | 2/2008 | Gale |
| 2008/0147164 A1 | 6/2008 | Gale et al. |

FOREIGN PATENT DOCUMENTS

| | | |
|---|---|---|
| WO | WO 99/55406 | 11/1999 |
| WO | WO 2006/117016 | 11/2006 |

OTHER PUBLICATIONS

International Search Report and the Written Opinion for PCT/US2008/077108 mailed Feb. 2, 2009, 6 pgs.

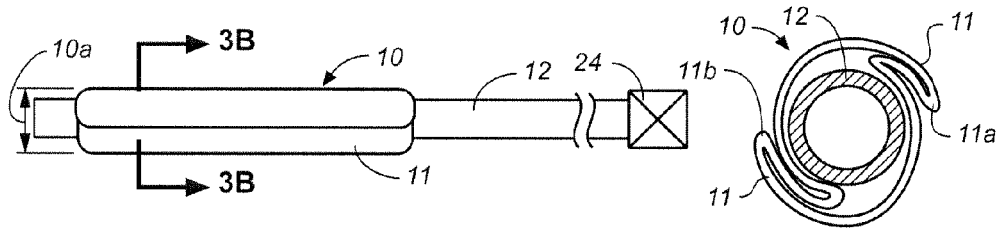
*FIG. 3A*  *FIG. 3B*
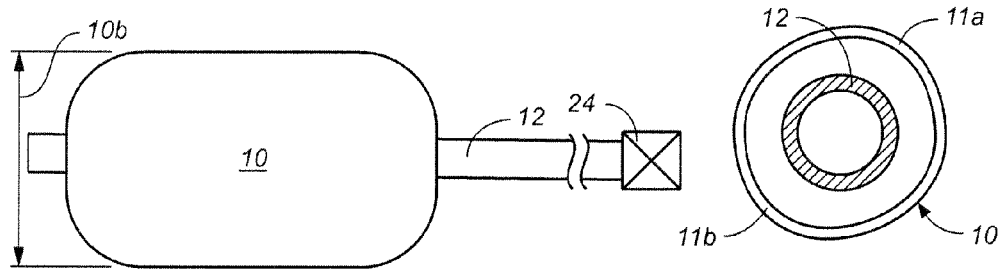
*FIG. 4A*  *FIG. 4B*
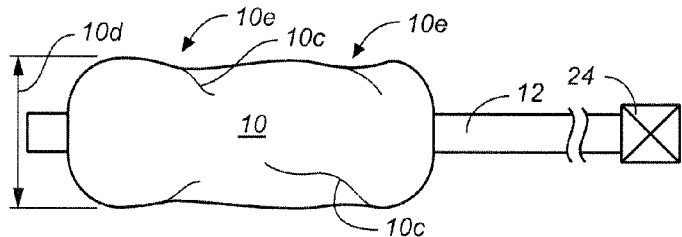
*FIG. 5*
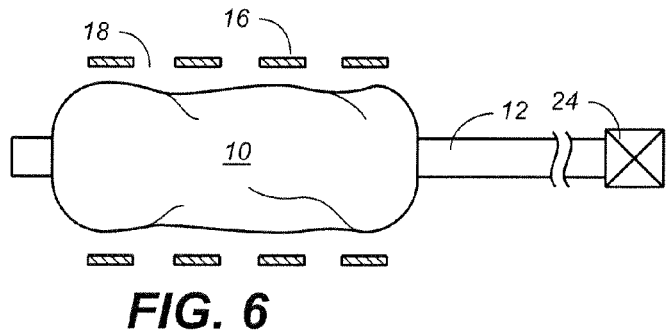
*FIG. 6*

STENT RETAINED ON A BALLOON CATHETER

The application is a divisional of U.S. application Ser. No. 13/252,965 filed Oct. 4, 2011, which is a continuation of U.S. application Ser. No. 11/864,834 filed Sep. 28, 2007, now U.S. Pat. No. 8,046,897, the contents of which are hereby incorporated by reference in their entirety for all purposes.

TECHNICAL FIELD

This invention relates to methods of crimping a stent on a balloon, and a stent secured to a catheter assembly.

BACKGROUND

A stent, as illustrated in FIG. 1, is an intravascular prosthesis that is delivered and implanted within a patient's vasculature or other bodily cavities and lumens by a balloon catheter. The structure of a stent is typically composed of scaffolding, substrate, or base material that includes a pattern or network of interconnecting structural elements often referred to in the art as struts or bar arms. Referring to FIG. 1, an exemplary stent 14 is illustrated. Stent 14 can include a plurality of struts 16 connected by linking struts 11, with interstitial spaces 18 located in between the struts. The plurality of struts 16 can be configured in an annular fashion in discrete "rows" such that they form a series of "rings" throughout the body of stent 14. Stents can be used in percutaneous transluminal coronary angioplasty (PTCA) or percutaneous transluminal angioplasty (PTA). Conventional stents and catheters are disclosed by U.S. Pat. Nos. 4,733,665, 4,800,882, 4,886,062, 5,514,154, 5,569,295, and 5,507,768. In advancing a stent through a body vessel to a deployment site, the stent must be able to securely maintain its axial as well as rotational position on the delivery catheter without translocating proximally or distally, and especially without becoming separated from the catheter. Stents that are not properly secured or retained to the catheter may slip and either be lost or be deployed in the wrong location. The stent must be "crimped" in such a way as to minimize or prevent distortion of the stent and to thereby prevent abrasion and/or reduce trauma to the vessel walls.

Generally, stent crimping is the act of affixing the stent to the delivery catheter or delivery balloon so that it remains affixed to the catheter or balloon until the physician desires to deliver the stent at the treatment site. Current stent crimping technology is sophisticated. Examples of such technology which are known by one of ordinary skill in the art include a roll crimper; a collet crimper; and an iris or sliding-wedge crimper. To use a roll crimper, first the stent is slid loosely onto the balloon portion of the catheter. This assembly is placed between the plates of the roll crimper. With an automated roll crimper, the plates come together and apply a specified amount of force. They then move back and forth a set distance in a direction that is perpendicular to the catheter. The catheter rolls back and forth under this motion, and the diameter of the stent is reduced. The process can be broken down into more than one step, each with its own level of force, translational distance, and number of cycles. This process imparts a great deal of shear to the stent in a direction perpendicular to the catheter or catheter wall. Furthermore, as the stent is crimped, there is additional relative motion between the stent surface and the crimping plates.

The collet crimper is equally conceptually simple. A standard drill-chuck collet is equipped with several pie-piece-shaped jaws. These jaws move in a radial direction as an outer ring is turned. To use this crimper, a stent is loosely placed onto the balloon portion of a catheter and inserted in the center space between the jaws. Turning the outer ring causes the jaws to move inward. An issue with this device is determining or designing the crimping endpoint. One scheme is to engineer the jaws so that when they completely close, they touch and a center hole of a known diameter remains. Using this approach, turning the collet until the jaws abut each other crimps the stent to the known outer diameter. While this seems ideal, it can lead to problems. Stent struts have a tolerance on their thickness. Additionally, the process of folding non-compliant balloons is not exactly reproducible. Consequently, the collet crimper exerts a different amount of force on each stent in order to achieve the same final dimension. Unless this force, and the final crimped diameter, is carefully chosen, the variability of the stent and balloon dimensions can yield stent or balloon damage.

In the sliding wedge or iris crimper, adjacent pie-piece-shaped sections move inward and twist, much like the leaves in a camera aperture. This crimper can be engineered to have two different types of endpoints. It can stop at a final diameter, or it can apply a fixed force and allow the final diameter to float. From the discussion on the collet crimper, there are advantages in applying a fixed level of force as variability in strut and balloon dimension will not change the crimping force. The sliding wedges impart primarily normal forces. As the wedges slide over each other, they impart some tangential force. Lastly, the sliding wedge crimper presents a nearly cylindrical inner surface to the stent, even as it crimps. This means the crimping loads are distributed over the entire outer surface of the stent.

All current stent crimping methods were developed for all-metal stents. Stent metals, such as stainless steel, are durable and can take abuse. When crimping is too severe, it usually damages the underlying balloon, not the metal stent. But polymeric stents present different challenges. A polymer stent requires relatively wider struts than metal stents so as to provide suitable mechanical properties, such as radial strength. At the crimping stage, less space is provided between the struts which can result in worse stent retention than a metallic stent. Moreover, the use of high processing temperature during the crimping process to enhance stent retention may not be possible as a polymeric stent may have a glass transition temperature between 40-60 degrees Celsius. Higher processing temperatures may cause the stent to lose some of its preferred mechanical properties.

Polymeric stents can also be more susceptible to crack propagation during crimping or expansion by a balloon. When a polymeric stent is placed on a balloon and a crimping pressure applied, the load on the struts can vary significantly. A significant cause for this load variation is the balloon surface, which due to its variation in surface geometry and stiffness properties over the surface imposes non-uniform reaction forces to crimping against the stent luminal surface. As the stent is pressed into the balloon surface, different stent struts will experience different loadings because the balloon does not everywhere have the same stiffness properties, i.e., some areas are less compliant than others. Moreover, the balloon surface is generally not smooth. As such, bumps or mounds over the balloon surface, especially in areas of relatively high stiffness, can produce different loadings across the stent body. For example, when a stent is crimped on a non-compliant balloon having folded wings or pleats, there can be noticeable bumps or mounds in the areas where the material is folded. Moreover, the stiffness in these areas, i.e., where the balloon material is folded over itself, can be noticeable higher than in areas distal from the folds. Variations in the surface geometry of the balloon and/or stiffness about the circumference and/or length of the balloon can lead to high stress concentrations resulting in twisting, bending, warping of individual struts or segments of the stent. Excessive loading in areas near corners, especially corners having surface imperfections created during the stent making process (typically a high stress area), can result in propagation of micro cracks leading to a significant reduction in strength or outright failure of a strut when the stent is expanded to its full diameter by the balloon.

The present invention provides a novel method of crimping a stent, more specifically a polymeric stent on an expandable member or a balloon, and a novel apparatus for delivery of a stent on a balloon catheter.

SUMMARY

In accordance with one embodiment, a method of crimping a stent on a balloon of a catheter assembly includes inflating a balloon, deflating the balloon, disposing the stent over the balloon after deflating the balloon, and then crimping the stent to the balloon. The balloon may be inflated to an intermediate pressure, maximum pressure, or hyper-inflated pressure for the balloon before being deflated. Various crimping procedures known in the art may be used. In some embodiments, the crimping procedure may include a step in which the balloon is re-inflated when the stent is disposed over the balloon. In some embodiments, the deflating step may deflate the balloon to about atmospheric pressure.

In some embodiments, the act of inflating the balloon inflates a balloon configured in a collapsed configuration, such that the balloon has prearranged folds that are heat set. When the balloon is inflated, the heat set folds are removed, or substantially removed from the balloon. When the balloon is deflated, the balloon may partially reform the folds.

In another embodiment, a method of securing a stent on a balloon of a catheter assembly, the balloon having prearranged folds when configured in a collapsed configuration, includes the steps of inflating the balloon such that the folds are substantially or completely removed, and crimping the stent to the balloon after the folds are substantially or completely removed. In some embodiments, the balloon is configured in a collapsed configuration, the folds are such as to form shape memory in a membrane of the balloon, and the crimping step includes crimping the stent to the balloon configured such that a portion of the shape memory in the balloon is still present in the membrane. During the crimping step, the balloon may be compressed such that at least a portion of the folds present in the collapsed configuration are replaced by irregular folds.

According to another embodiment, a method of crimping a stent to a balloon includes the steps of inflating the balloon from an initial diameter to a final diameter, deflating the balloon such that the balloon forms a relaxed state, and after deflating the balloon, crimping the stent to the balloon. In some embodiments, the balloon pressure is reduced to about atmospheric when the balloon is in the relaxed state.

According to another embodiment, a balloon catheter includes a balloon of the type having a membrane predisposed to form at least one prearranged fold when in a collapsed configuration, the balloon being configured in a compressed configuration such that the at least one prearranged fold is replaced by at least one irregular fold in the compressed configuration, and a stent secured to the balloon.

According to another embodiment, a balloon catheter includes a balloon of the type configured to have at least one prearranged fold when in a collapsed configuration, and a stent compressed onto the balloon such that the balloon is devoid of the at least one prearranged fold. In some embodiments, the balloon is a non-compliant balloon. In some embodiments, the balloon has a plurality of prearranged folds when configured in a collapsed configuration, and when the stent is compressed onto the balloon the plurality of folds are replaced by folds resulting from the compression of the stent onto the balloon.

In one aspect, embodiments of a method and apparatus are disclosed that can reduce the instances of failed or bent stent struts during crimping and/or subsequent expansion of the stent by a balloon catheter. In another aspect, the disclosure provides a method and apparatus to improve stent retention and uniform expansion of the stent. In another aspect, the disclosure provides a method and apparatus for an improved manufacturing procedure, such as elimination of time consuming steps and improved quality control when stents are secured to a balloon.

DESCRIPTION OF FIGURES

The figures have not been drawn to scale and portions thereof have been under or over emphasized for illustrative purposes.

FIGS. 3A and 3B show side and axial views, respectively, of a balloon catheter with a balloon configured in a collapsed configuration;

FIGS. 4A and 4B show side and axial views, respectively, of the balloon when inflated.

FIG. 5 illustrates the balloon in FIG. 4A after having being deflated;

FIG. 6 illustrates a side view of the balloon of FIG. 5 with a stent disposed over the balloon;

DESCRIPTION

Embodiments of the stent crimping methods of the invention disclosed herein are suitable to adequately and uniformly crimp a balloon expandable stent onto a balloon or expandable member of a catheter assembly. The embodiments of the invention may also be applicable to stent-grafts. In one embodiment, the method of the present invention is particularly directed to crimping of a biodegradable, polymeric stent on a balloon of a catheter assembly. A biodegradable polymer stent has many advantages over non-biodegradable metal stents, including the ability to be disposed in the body only for the duration of time until the intended function of the stent has been performed.

Crimping of polymer stents has proven more challenging than metal stents. A polymer, having generally less favorable stress/strain properties than a metal, is more likely to become damaged during crimping as compared to a metal stent. High stresses are better handled by a metal stent due to its inherent material properties. Polymeric stents, however, can fracture when faced with a similar crimp loading.

As such, a polymer stent is generally less tolerant of localized high stresses resulting from non-uniform applied loads that can occur when the stent is pressed into a balloon.

Figure 1:
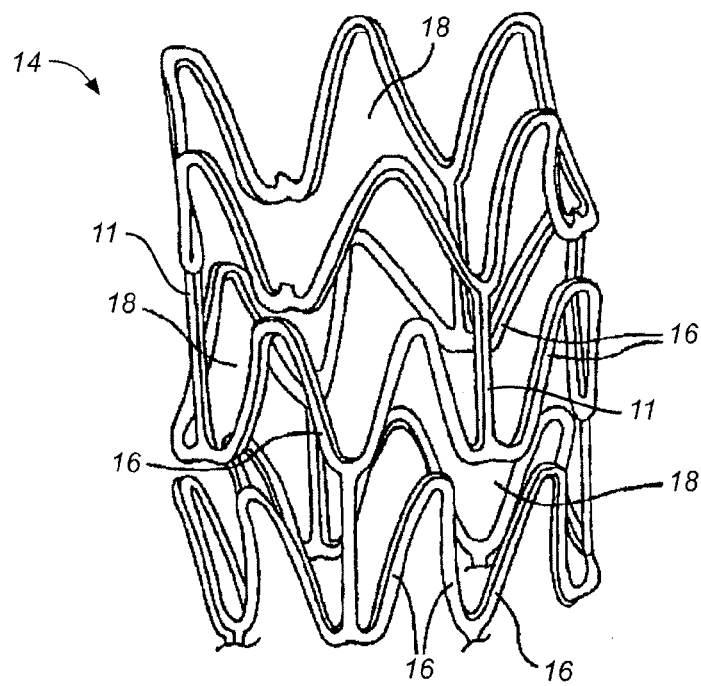
FIG. 1 is a perspective view of a stent.
Figure 2A:
FIGS. 2A, 2B, 2C and 2D illustrate crimped stents that have struts misaligned by a crimping process.
Figure 2B:
Figure 2C:
Figure 2D:
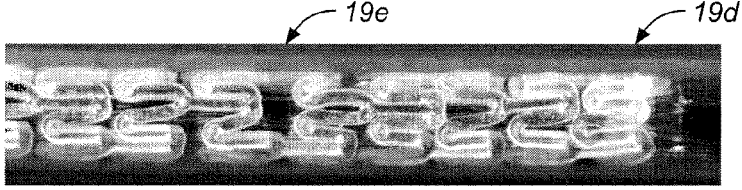

FIGS. 2A, 2B, 2C and 2D illustrate four different polymeric stents crimped to balloons. Ideally, all struts for this particular stent should extend parallel to the longitudinal axis after crimping. However, in each of these figures one or more stent struts or rings has been twisted, bent or misaligned in an desired way, i.e., deformed such that struts do not extend parallel to the longitudinal axis as intended. FIG. 2A shows an over-compressed ring 19a at the end of the stent in which struts abut each other and are twisted downward. The stent in FIG. 2B shows a similar situation for the struts of ring 19b, also located at the end. Additionally, it can be seen in the stent of FIG. 2B that the rings adjacent ring 19b are twisted upward. In FIG. 4C it can be seen that an entire row of struts 19c are twisted upwards or downwards. As mentioned above, it is preferred by design that all struts for this stent extend parallel to the stent longitudinal axis when the stent is crimped to the balloon. FIG. 2D shows a similar undesired deformity for ring 19d. Additionally, ring 19e located closer to the center of the stent in FIG. 2D also has an desired twist in its struts. When these stents are expanded by the balloon, some of the aforementioned misalignment, twisting or bending may be undone. In other cases balloon expansion may not straighten out these struts and/or rings. Worse yet, balloon expansion may cause one or more of the misaligned struts to fail. In these cases, it is believed that the above noted undesirable deformations were due in large part to variations in surface contour and/or compliance characteristics of the balloon surface which received the stent during crimping.

Retention of a polymer stent on a balloon of a delivery catheter while it is passed through a body lumen has proven more challenging than that of a metallic stent. Polymer stents can require wider struts than metal stents so as to provide suitable mechanical properties, such as radial strength, for the stent. At the crimping stage, less space is provided between the struts which can result in worse stent retention than a metallic stent. Moreover, the use of high processing temperature during the crimping process to enhance stent retention may not be possible as a polymeric stent may have a glass transition temperature close to body temperature. Higher processing temperatures may cause the polymeric stent to lose some of its preferred mechanical properties.

Additionally, stents can shift on a balloon during a crimping process. For example, if the balloon is inflated while the stent is disposed over the balloon in a crimping machine, the stent longitudinal axis can become skewed from the balloon longitudinal axis, or the stent can shift axially. If this should occur, the stent and balloon will need to be removed from the crimping machine, the stent re-centered and the crimping protocol re-started. It is believed that this misalignment is usually due to non-uniform expansion characteristics of folded balloons. For example, some wings or pleats of a folded balloon may unfold faster than others. This can produce a net torque on the stent over its length, or unequal radial expansion when the balloon is viewed in a plane perpendicular to the longitudinal axis. Friction between layers or inconsistent pre-loading of folds when wings are formed are factors contributing to uneven balloon expansion.

FIGS. 3A and 3B show side and cross-sectional views of an expandable member, such as a balloon 10, integrated at a distal end of a catheter assembly 12. The catheter 12 includes a valve 24 to relieve balloon pressure and a pressure source (not shown). In some embodiments, the balloon 10 is intended to include any type of enclosed member such as an elastic type member that is selectively inflatable to dilate from a collapsed configuration to a desired and controlled expanded configuration. The balloon 10 should also be capable of being deflated to a reduced profile or back to its original collapsed configuration. The balloon 10 can be made from any suitable type of material and can be of any thickness so long as the ability to crimp the stent onto the balloon and optimum performance capabilities of the balloon are not adversely compromised. Performance properties include, for example, high burst strength, good flexibility, high resistance to fatigue, an ability to fold, and ability to cross and re-cross a desired region of treatment or an occluded region in a bodily lumen, and a low susceptibility to defects caused by handling and crimping, among other possibilities.

The balloon is illustrated in FIG. 3A in a collapsed configuration. The collapsed configuration can be the configuration that is conventionally used during the process of crimping of a stent on a balloon. In the collapsed configuration, the balloon 10 includes no liquid or gas in the internal chamber of the balloon 10. Such collapsed configuration can be the configuration of introduction and navigation of the balloon 10 in the vascular system of a patient and may be referred to as a configuration of the balloon in which the balloon has a minimum profile. The diameter 10a of the balloon 10 is then the minimum diameter for the balloon. The balloon can be folded when in the collapsed configuration, which is the typical case for collapsed non-compliant balloons. The folds in a collapsed configuration are prearranged folds, meaning that the balloon material is folded according to a particular pattern or design intended to achieve an objective, e.g., a minimum profile. The folding is undertaken in an orderly manner either by hand or by a machine process. The folded parts of the balloons are often referred to as wings or pleats. The balloon is then typically heat set to hold the wings or pleats in place. For non-compliant balloons, which use material that is essentially non-elastic within the balloon operating ranges, the balloon inflates when wings or pleats have unfolded. As such, non-compliant balloons sometimes have several tightly wound layers of prearranged folded balloon material when in the collapsed configuration in order to achieve a minimum profile or diameter for the balloon.

FIG. 3B depicts the balloon 10 folded in such a manner so as to create two opposing, prearranged wings or pleats 11, each having prearranged kinks or folds 11a, 11b. In other embodiments, the catheter may have a balloon that has more than two wings. Balloons may be folded in a spiral or accordion like fashion, each approach to achieve a specific objective, e.g., low profile, uniform expansion, reduced manufacturing complexity or quality control. Once folded, the balloon 10 is heat set so that folds 11 are maintained. The heat set can be such that if the balloon pressure is increased enough to unfold the wings, and then the balloon pressure is reduced back to below atmospheric, the balloon will take the same shape as it had prior to inflation.

Embodiments of the invention include the known types of collapsed balloon configurations, provided they are capable of being crimped to a stent and then delivered to a site within the body according to the disclosure. Stents crimped to compliant and semi-compliant balloons may also benefit from the teachings of the invention. As such, stent delivery systems that use compliant and semi-compliant balloons are also considered within the scope of the invention. Balloon folding techniques and balloon types are discussed in greater detail in U.S. Pat. Nos. 5,556,383, 6,488,688 and U.S. Pub. No. 2005/0244533, the entire contents of which are incorporated by reference as examples of the state of the art in this area.

Methods according to some embodiments of the invention can include an inflation of the balloon from a collapsed configuration to an inflated state, a deflation of the balloon from the inflated state, and then crimping the stent to the balloon using any known crimping procedure, provided those procedures are not inconsistent with the disclosure. The suitable choices for the crimping device and/or procedure that may be used in connection with embodiments of the invention will be understood from the disclosure. The crimping, inflation and deflation aspects of the disclosure may each include additional steps or processes, some of which are disclosed herein while others would be readily apparent based on the disclosure.

According to a disclosed embodiment, a method for securing a stent to a balloon begins with inflation of the balloon 10 to an inflated state, as shown in FIG. 4A. In this state, the balloon 10 has an inflated diameter 10b. In some embodiments, all balloon folds are removed, substantially all balloon folds are removed, the balloon is fully unfolded or the balloon is substantially fully unfolded in the inflated state. In some embodiments, the balloon takes its final expanded shape, e.g., cylindrical, or substantially its final expanded shape, when the balloon is in the inflated state.

The inflated shape may also be understood in terms of the internal balloon pressure when the balloon is in the inflated state, instead of the balloon shape. The balloon 10 is inflated by a pressure source (not shown) connected to the proximal end of the catheter 12 in FIG. 4A. The inflated state may be achieved after the balloon is inflated to a maximum intended pressure or design pressure, an intermediate pressure, a hyper-inflated pressure. In some embodiments, a balloon inflated to any pressure that causes the balloon to at least partially expand places the balloon in an inflated state. Such embodiments include those in which the pressure is sufficient to break any friction between folded wings in the balloon material. A maximum intended pressure refers to a balloon pressure considered the highest from a standpoint of acceptable risk of damage to the balloon as prescribed under a standard medical protocol. A balloon manufacturer can supply this information or it can be determined using known methods. The maximum intended pressure may also refer to the diameter of the balloon when fully expanded, e.g., diameter 10b in FIG. 4A. In the case of non-compliant balloon this would correspond to the outer balloon diameter after the wings have been fully unfolded. The maximum intended pressure may also refer to the balloon pressure that produces approximately the largest diameter designated for clinical use, in the case of compliant or semi-compliant balloons.

In some embodiments, the inflated state may correspond to a hyper-inflated balloon. Hyper-inflation is defined as any pressure or size above the intended expanded configuration but less than a pressure or size that creates an unacceptable risk that the balloon will be damaged. For example, a hyper-inflated pressure for a 3.0 mm balloon would be an applied balloon pressure that causes the balloon to expand to 3.5 mm or 4.0 mm, which diameters should usually not cause balloon damage. Balloon diameter tolerances depend on the type of balloon and the material from which the balloon is made, among other factors. The manufacturer of the balloon can provide such information to a user, for example.

An intermediate pressure refers to a pressure that, while not reaching the maximum intended pressure, is sufficient to substantially remove the folds or kinks in the balloon material when the balloon was in the collapsed configuration, or places the balloon in a substantially unfolded configuration. For example, an intermediate pressure for the balloon 10 would be the pressure sufficient to substantially undo the kinks 11a and 11b caused by the folded, collapsed configuration in FIG. 3B, but less than the maximum intended pressure for balloon 10. FIG. 4B depicts the balloon 10 when inflated to an intermediate pressure. Thus, FIG. 4B is one example of a balloon were the folds are substantially removed. The places on the balloon material where the balloon material was folded over itself, i.e., kinks or folds 11a, 11b, cannot be identified. Also, the balloon has taken an essentially circular shape.

A softening agent can be applied to the balloon surface before, during or after the inflated state has been reached. This can make the balloon surface softer or more pliable and can also help to work-out some of the shape memory properties of the balloon material remaining from the heat set. The term "work-out" is intended to mean the application of a loading, e.g., inflating, coating, and/or heating of the balloon to reduce or undo the shape memory in the material that resulted from the balloon folds in the collapsed configuration, such as folds that were heat set in place. The balloon may be inflated and deflated several times as this may also help to work-out the shape memory properties. The deflated pressure for these embodiments may be near the collapsed configuration or relatively close to the less-than the intended maximum pressure, the maximum pressure or the hyper-inflated pressure level. For example, the inflated pressure of the balloon may be cycled between ambient pressure and the intended maximum pressure, the intermediate pressure and the maximum pressure, etc.

The temperature of the liquid or gas used to expand the balloon to the inflated state may be adjusted to other than ambient or room temperature, and the inflated state may be maintained for a period of time. For example, the balloon may be expanded or contracted by a heated, chilled or cold fluid, respectively. In some embodiments, a heated fluid can be defined as above 25 deg. C. In some embodiments, the temperature can be below 200 deg. C., or alternatively below 150 deg. C., or alternatively below 100 deg. C., or alternatively below 75 deg. C. In some embodiments, the temperature can be between 25 deg. C. and 100 deg. C. A cooled fluid can mean below 25 deg. C. A chilled fluid can mean below 0 deg. C.

Subsequent to configuring the balloon 10 in an inflated state, the balloon is placed in a relaxed state, as depicted in FIG. 5. For this embodiment, the balloon 10 has a maximum radial extent 10d, a surface having random depressions 10e and irregular or random folds 10c. A relaxed state is intended to mean the shape that the balloon takes after the pressure in the balloon is reduced from the inflated state. In some embodiments the relaxed state is such that when the stent is crimped to the balloon, new folds or creases replace prearranged folds from the collapsed configuration. In some embodiments, the balloon is maintained at a pressure, such as greater than about one atmosphere for a relaxed state. In this case, the stent may be crimped onto the balloon while the internal pressure is allowed to release.

In some embodiments, the relaxed state corresponds to the balloon surface showing generally the same wings that it had in the collapsed configuration as a result of shape memory in the membrane, but the wings are partially formed. When the stent is subsequently crimped to the balloon, irregular or random folds form as a result of the circumferential forces during crimping, in spite of the presence of the partially reformed wings. In some embodiments, some of the prearranged folds can be found on the balloon after crimping. In some embodiments, the prearranged folds are no longer present after crimping.

Figure 8:
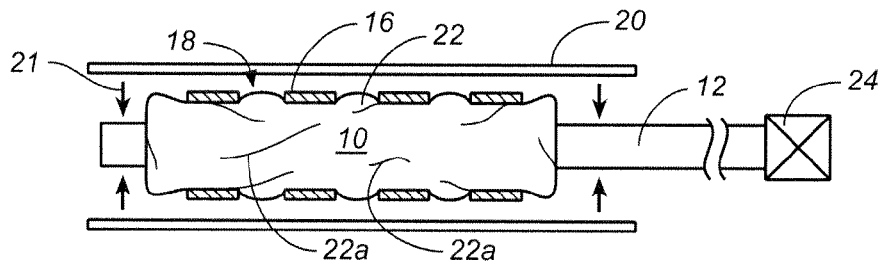

For example, the relaxed state for balloon 10 can correspond to a shape that shows a partial formation of the two spiral-wound wings 11 in FIG. 3B, but when the stent is crimped to the balloon 10 those wings 11 are no longer present. Instead, the prearranged folds are replaced by irregular or random folds 22a that form as the stent 14 bears down on the balloon during crimping, as depicted in FIG. 8. Irregular or random folds or wrinkles is intended to mean folds or wrinkles that are not formed in a prearranged manner. In some embodiments, irregular or random folds or wrinkles, e.g., folds 22a (FIG. 8) or 10e (FIG. 5) describe the appearance of the balloon when left to form folds or wrinkles, either as the balloon membrane collapses under its own weight, e.g., folds 10e in FIG. 5, or when prearranged folds from the collapsed configuration are replaced by new folds or wrinkles during crimping, e.g., folds 22e in FIG. 8. In some embodiments the surface of the balloon may have substantially all, or only a portion of the folds from the collapsed configuration present in the relaxed state. In some embodiments, the relaxed state is such that when the stent is crimped to the balloon, heat set folds are not reformed when the stent is crimped to the balloon. Rather, new creases or folds replace the heat set folds.

A balloon pressure for the relaxed state may be arrived at by simply opening the valve 24 to allow fluid to exit from the balloon, or by a controlled release of the fluid. The fluid may be released continuously or in stages, e.g., 1 atm per minute, etc. In some embodiments, a relaxed state corresponds to the shape of the balloon when the pressure inside is at about atmospheric pressure. In other embodiments the relaxed state is achieved when the balloon pressure is decreased to a pressure less than the pressure corresponding to the inflated state, e.g., 10-30%, less than 50%, 50-60%, 60-80%, 80-90%. In some embodiments, the balloon pressure may be less than the maximum intended pressure but higher than ambient pressure. In some embodiments, the balloon is allowed to deflate only by an amount sufficient to enable a stent to be easily placed over the balloon, or so that a stent may be snugly fit over the balloon.

In some embodiments, the aforementioned inflating and deflating steps may be repeated one or more times in order to arrive at a desired relaxed state. These additional steps, in addition to other loadings of the balloon intended to workout shape memory in the material, as discussed earlier, may be advantageous to further promote a more uniform expansion of the balloon. A more uniform expansion of the balloon is desirable because the balloon should be less likely to expand the stent in a irregular manner. Further, a more uniform expansion should equate to more uniform stiffness properties of the balloon over its surface and, in particular, in those areas proximal to bumps or mounds as compared to areas distal from bumps or mounds. As such, when the stent is pressed into the balloon during crimping the localized stress concentrations should not be as severe. This should reduce instances of crack propagation in a stent strut and/or undesired plastic deformations of the crimped stent.

Figure 7:
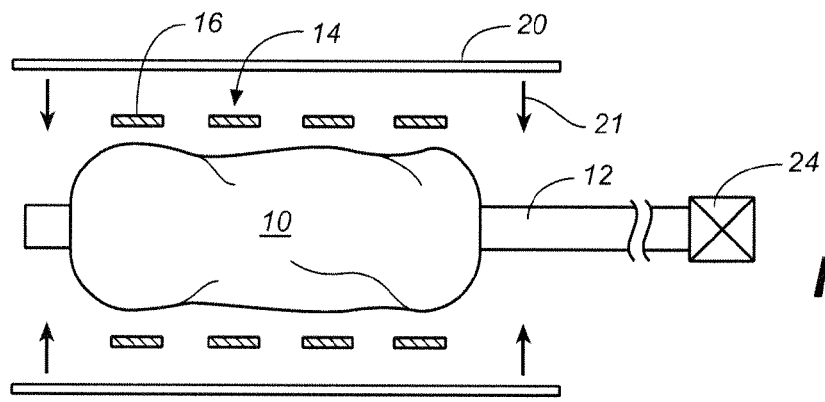
FIGS. 7 and 8 illustrate a crimping step for the stent to the balloon and the balloon and stent following crimping.

After the deflating step, the stent is placed over the balloon, which is in a relaxed state. This stage of the process is depicted in FIG. 6. The stent has struts 16 separated by gaps 18. As indicated above, in some embodiments the balloon is inflated to atmospheric pressure or above atmospheric when in a relaxed state. The balloon may also be filled with a liquid when in the relaxed state. The balloon pressure may be up to an amount that allows the stent to be loosely placed on the balloon or snugly fit on the balloon. FIG. 7 depicts the stent 14 on the balloon 10, and the balloon 10 in a relaxed state when in a crimping device 20. The crimping device is designed to apply uniform radial compressive forces 21 to the outer stent surface sufficient to plastically deform the stent. The effect of the applied force 21 is shown in FIG. 8. As depicted in FIG. 9, the balloon 10 has irregular or random folds 22a but not the prearranged folds 11 present in the balloon's collapsed configuration (FIGS. 3A and 3B).

The stent 14 may be fully crimped onto the balloon 10 in one step, or the stent 10 may be crimped on the balloon using any multi-step protocol known in the art provided it can be used or adapted for use consistent with the teachings of the invention. Crimping can be defined as the process of mounting, fastening or securing a stent on a balloon. The stent can then be fixedly carried by the balloon and deployed by inflation and subsequent withdrawal of the balloon in order to implant the stent at a target site, such as a region of stenosis. The crimp process can include selectively, radially compressing or applying pressure for positioning a stent on a balloon of a catheter assembly or an expandable delivery member of a catheter assembly. The compression or radial pressure during crimping can be segmented or uniform across the length and/or circumference of the stent. The application of pressure by the crimping device 20 can be continuous or applied in an intermittent or step-wise fashion. In these embodiments, the balloon can be deflated and re-inflated until a final crimp configuration has been achieved.

The stent may be partially crimped on the balloon, followed by the balloon pressure being increased. The balloon may also be heated prior or during crimping. The final configuration of the stent 14 as fully crimped is illustrated in FIG. 8. Protrusions 22 of the balloon are disposed in the gaps 18 of the stent struts 16. It has been found that in some embodiments, as a result of the aforementioned effects on balloon stiffness resulting from the disclosed inflation and deflation steps, i.e., more uniform stiffness properties, a stent's slip resistance from the balloon following crimping can be improved. In these embodiments, the balloon material is more capable of protruding into the gaps 18 before or during crimping. And when disposed in the gaps 18, the protrusions 22 may be used to increase the slip resistance of the stent. In some embodiments, balloon material may more readily slip into gaps 18 by maintaining the balloon 10 in an inflated state while the stent is crimped. The valve 24 is regulated during crimping in order to relieve the balloon 10 pressure at a suitable rate as the stent continues to bear down on the balloon. For example, the pressure may be relieved at such a rate as to allow the balloon material sufficient time to fill or slip into the gaps but without increasing the balloon pressure beyond a safe limit. In one embodiment, the protrusions 22 preferably do not extend beyond the outer surface of the struts 16, while in other embodiments the protrusions 22 may extend beyond the outer surface of the struts 16. In some embodiments, the balloon may be heated to promote expansion of the balloon material into gaps 18 before or during crimping. When the balloon material is disposed within the gaps 18, the balloon wall or membrane may become wedged, lodged, squeezed, or pinched between the struts 16 when the crimping process is completed.

In some embodiments, the crimping device can hold the balloon pressure at a desired pressure or temperature for a period of time prior to relief of pressure. The process of crimping can also include, unless otherwise specifically indicated, modifications made to the stent and/or balloon prior, during or subsequent to the application of crimping pressure that is directed to retention of the stent on the balloon. For example, the balloon can have an adhesive coating to improve the retention of the stent on the balloon. In some embodiments, the balloon can be dipped into a fluid or solvent such as acetone before sliding the stent on the balloon in order to soften the balloon material. This makes it easier for the balloon material to squeeze into the space between the stent struts. The solvents, such as acetone, may also partially dissolve the surface of the stent or coating on the stent allowing for better adhesion between the stent and the balloon. In some embodiments, a softening fluid can be used that is a non-solvent for the stent or the coating on the stent.

During the crimping stage, as with the inflation stage, the balloon 10 can be inflated by application of a fluid or a gas at a temperature other than ambient. In one embodiment, a heated fluid or gas is used when the stent is crimped onto a deflating balloon. In some embodiments, heated can be defined as above 25 deg. C. In some embodiments, the temperature can be below 200 deg. C., or alternatively below 150 deg. C., or alternatively below 100 deg. C., or alternatively below 75 deg. C. In some embodiments, the temperature can be between 25 deg. C. and 100 deg. C. In some embodiments, the temperature is equal to or above the glass transition temperature (Tg) of a polymer of the stent body or a polymer of the stent coating (if applicable). In some embodiments, the temperature is equal to or above Tg but less than a melting temperature of a polymer of the stent body or a polymer of coating over the stent body. In some embodiments, a cooled or chilled fluid or gas can be used to inflate the balloon. Cooled can mean below 25 deg. C. Chilled can mean below 0 deg. C.

In some embodiments, the outer surface of the balloon or the inner surface of a stent can include a coating, such as an adhesive coating, a drug delivery coating, a protective coating, a polymeric coating. If it is desirable instead to increase, not decrease friction, a heat activated adhesive coating may be used. For example, a polymer having a melting or glass transition temperature below that of a stent and balloon may be applied to the stent or balloon surfaces, and the stent and balloon heated to activate the coating so that the friction between stent and balloon is increased.

Figure 9A:
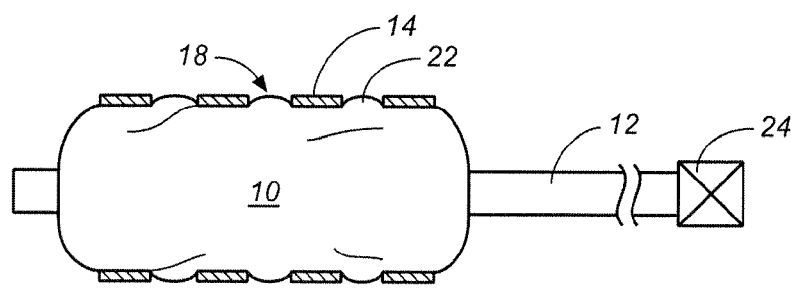
FIGS. 9A and 9B illustrate an alternative crimping procedure.
Figure 9B:
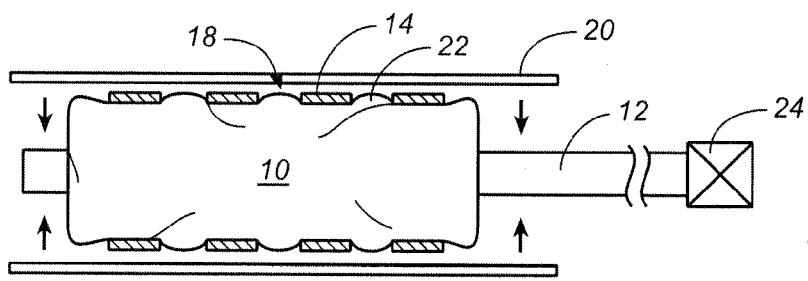

In another embodiment, the stent may be partially crimped and the balloon expanded by application of heat or inflated into the stent so that the balloon material begins to protrude into the gaps 18 prior to a final crimping step. FIG. 9A illustrates the balloon 10 and the stent 14 in the partially crimped configuration. FIG. 9B illustrates the final crimped configuration for this embodiment. It has been found that when the aforementioned inflating and deflating steps are carried out prior to this crimping protocol, the stent does not become skewed relative to the catheter or shifted axially along the balloon. The explanation for this behavior is understood in light of the previous discussion.

The stent body itself is preferably made from a polymeric material such as one or a combination of polymers. In some embodiments, such body can be made from a combination of polymeric and metallic material(s). In some embodiments, the stent is biodegradable. Both polymers and metallic materials can be biodegradable. In one preferred embodiment, the stent is completely or exclusively made from a polymeric material or combination of polymeric materials, more specifically biodegradable polymer(s). A polymeric stent can include some metallic components for allowing the stent to be viewed during the procedure; however, the amount of material is insignificant, does not impart any structural function to the stent, or for viewing means only such that the stent is in essence made from a polymeric material or combination of polymers as is understood by one having ordinary skill in the art. In some embodiments, metallic stents are completely excluded from any of the embodiments of this invention. Metallic stents have a stent body (i.e., struts or structural elements) made mostly or completely from a metallic material such as a pure metal or an alloy. It should be noted that biodegradable is intended to include bioabsorbable, bioerodable, etc. unless otherwise specifically indicated.

In some embodiments, the stent can include a drug coating. The coating can be a pure drug or combination of drugs. The coating can include a polymeric carrier for the drug, either a single polymer or multiple polymers. The coating can be layered as is understood by one of ordinary skilled in the art.

The stent or the coating can be made from a material including, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly (glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating the stent include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

A metal stent may also be used in conjunction with the above-described embodiments. The stent can be made of a pure metal or a metal alloy such as, but not limited to, stainless steel (316L), "MP35N," "MP20N," tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Stents made from bioabsorbable or biostable polymers could also be used with the embodiments of the present invention.

EXAMPLE

Polymeric stents were crimped onto balloon catheters using a procedure consistent with the disclosure (hereinafter the "new crimping method"). For this test, a 3.0 mm non-compliant balloon was dilated from a collapsed configuration to an inflated state of between 12-20 psi, then deflated so that the stent internal pressure was about equal to atmospheric pressure. In this relaxed state, a laser cut polymeric stent (OD=0.136 in) was placed on the balloon and aligned between two marker bands. The stent and balloon were then placed into a crimping machine. The stent was then crimped to a designated diameter (0.053 in) in one step (from 0.136 in to 0.053 in) or several steps (from 0.136 in to 0.08 in, then to 0.053 in) in the range of 30 to 50 degrees Celsius. The crimping procedure included the steps of inflating the balloon before crimping, and after the stent was partially crimped to 0.08 in. The crimped stent was then sterilized by electronic beam radiation with a dose of about 25 kGray. The above procedure was performed for 30 stents. Only one of the crimped stents were observed to have very slight bent struts at one end after being crimped using the new crimping method, as observed under an optical microscope with 4× magnification. As a control group, a different lot of the 30 laser cut stents were crimped onto 3.0 mm non-compliant balloons using the same crimping procedure as above, but without inflating and deflating the balloon before crimping. In this group, seven stents with bent struts or uneven alignment were observed under the optical microscope at 4× magnification.

Ten stents crimped using the new crimping method, and ten stents from the control group were expanded by the balloon and subjected to accelerated aging (40 degrees Celsius) at 24 hour and 65 hour time points. The expanded stents from both groups were then inspected for cracks or fractures after being expanded by the balloon. For purposes of this test, the stents with designed expanded diameters of 3.0 mm were over-expanded to 3.5 mm, and then 4.0 mm diameters. TABLES 1 and 2 show the number of cracked and broken stents found in the stents crimped according to the new crimping method ("Lot B") versus the stents crimped for the control group ("Lot A").

TABLE 1

Expansion Results (24 hour accelerated aging time point)

| Expansion | | Deployed to 3.5 mm | | | Deployed to 4.0 mm | | |
|---|---|---|---|---|---|---|---|
| | Sample # | 25% | 50% | Broken | 25% | 50% | Broken |
| Lot A | 6 | 2 | 0 | 0 | 4 | 2 | 1 |
| | 28 | 2 | 1 | 0 | 2 | 1 | 3 |
| | 29 | 3 | 0 | 0 | 4 | 1 | 0 |
| | 34 | 13 | 7 | 0 | 16 | 7 | 2 |
| | 36 | 4 | 0 | 0 | 6 | 1 | 0 |
| Lot B | 26 | 2 | 0 | 0 | 5 | 1 | 0 |
| | 45 | 5 | 0 | 0 | 7 | 0 | 0 |
| | 46 | 2 | 0 | 0 | 4 | 1 | 0 |
| | 47 | 0 | 0 | 0 | 2 | 0 | 0 |
| | 48 | 0 | 0 | 0 | 0 | 0 | 0 |

TABLE 2

Expansion Results (65 hour accelerated aging time point)

| Expansion | | Deployed to 3.5 mm | | | Deployed to 4.0 mm | | |
|---|---|---|---|---|---|---|---|
| | Sample # | 25% | 50% | Broken | 25% | 50% | Broken |
| Lot A | 5 | 5 | 0 | 1 | 7 | 2 | 3 |
| | 20 | 5 | 3 | 0 | 9 | 2 | 7 |
| | 24 | 7 | 4 | 0 | 4 | 1 | 9 |
| | 32 | 8 | 4 | 0 | 10 | 1 | 7 |
| | 33 | 3 | 1 | 0 | 5 | 2 | 2 |
| Lot B | 27 | 2 | 0 | 0 | 5 | 0 | 0 |
| | 34 | 8 | 0 | 0 | 9 | 0 | 0 |
| | 38 | 4 | 0 | 0 | 4 | 1 | 1 |
| | 40 | 8 | 3 | 0 | 5 | 3 | 5 |
| | 51 | 5 | 0 | 0 | 7 | 0 | 0 |

"Sample #" indicates the particular sample from the respective lot. "25%" and "50%" refers to the length of a crack observed in a strut for a sample (as a percentage of the strut width). "Broken" indicates the number of broken struts following expansion for a sample. As evident from the data shown in TABLES 1 and 2, the new crimping method significantly reduces instances of cracked or broken struts after the crimped stent was expanded by the balloon, as compared to the control group.

TABLE 3 shows results of performance tests for the stents crimped using the new crimping method (Lot B) compared to the control group (Lot A). The data presented in this table show that the new crimping method does not produce any adverse effects on retention or slip resistance, recoil, radial strength and modulus of the stents as compared to the control group. The stent retention test was evaluated by a dislodgement test. Two out of the five of stents crimped using the new crimping method were found to have a much higher holding force.

TABLE 3

Recoil, retention, radial strength and modulus of stents

| | LOT A | | | | LOT B | | |
|---|---|---|---|---|---|---|---|
| Test | # of samples | Average | STD Dev | Test | # of samples | Average | STD Dev |
| Recoil | 5 | 8.6% | 2.1% | Recoil | 5 | 7.9% | 1.5% |
| % Length Change | | 3.9% | 2.7% | % Length Change | | 2.6% | 0.8% |
| Uniformity of Expansion | | 0.04 | 0.03 | Uniformity of Expansion | | 0.06 | 0.01 |
| Radial Strength | 5 | 7.978 | 0.290 | Radial Strength | 5 | 7.726 | 0.315 |

TABLE 3-continued

Recoil, retention, radial strength and modulus of stents

| | LOT A | | | | LOT B | | |
|---|---|---|---|---|---|---|---|
| Test | # of samples | Average | STD Dev | Test | # of samples | Average | STD Dev |
| Modulus | | 657.7 | 105.246 | Modulus | | 677.9 | 85.334 |
| Dislodgement test | 5 | 1.2566 | 0.192361119 | Dislodgement test | 5 | 1.2834 | 0.085909 |

What is claimed is:

1. A method for making a medical device, comprising:
providing a balloon having a shape memory forming prearranged pleats or wings, wherein the prearranged pleats or wings have kinks;
working-out the shape memory including removing the kink of at least one of the prearranged pleats or wings, thereby replacing the at least one of the prearranged pleats or wings with random folds; and
crimping a stent including plastically deforming the stent onto the balloon while the balloon has the random folds.

2. The method of claim 1, wherein the stent comprises a polymer having a glass transition temperature of between 40 and 60 degrees Celsius.

3. The method of claim 1, wherein the working-out the shape memory includes removing at least one heat set pleat or wing that is folded in a spiral or accordion-like fashion.

4. The method of claim 3, wherein the balloon shape memory is worked-out by inflating and deflating the balloon or applying a fluid to a surface of the balloon.

5. The method of claim 1, wherein when the stent is crimped to the balloon all of the prearranged pleats or wings are replaced by random folds.

6. The method of claim 1,
wherein the balloon is a 3.0 mm balloon; and
wherein the crimped stent has an outer diameter of 0.053 inches.

7. The method of claim 1, wherein the balloon is a non-compliant or semi-compliant balloon.

8. The method of claim 1, wherein a membrane of the worked-out balloon is folded over itself in an irregular manner when the stent has a final crimping diameter.

9. The method of claim 1, wherein the stent is crimped to the balloon using an iris-type crimping mechanism.

10. (A method for making a medical device, comprising:
providing a balloon having a shape memory forming prearranged folds;
working-out the shape memory, whereby at least one of the prearranged folds is replaced by random folds;
placing a stent over the balloon after working out the shape memory, wherein the balloon is at least partially inflated when the stent is placed over the balloon; and
crimping the stent including plastically deforming the stent onto the balloon while the balloon has the random folds.

11. The method of claim 10, wherein the balloon is inflated such that the stent is snugly fit over the inflated balloon when the stent is placed over the inflated balloon.

12. The method of claim 10, wherein the balloon is inflated such that the stent is loosely fit over the inflated balloon when the stent is placed over the inflated balloon.

13. The method of claim 1, wherein the working out the shape memory includes inflating and deflating the balloon several times.

14. The method of claim 1, wherein the crimping step includes using an iris crimper to plastically deform the stent onto the balloon, wherein the iris crimper applies a continuous crimping force until the stent reaches a final crimp diameter.

15. The method of claim 1, wherein the crimping step includes using an iris crimper to plastically deform the stent onto the balloon, wherein the iris crimper applies a crimping force in an intermittent step-wise fashion until the stent reaches a final crimp diameter.

16. The method of claim 1, wherein the stent is a laser cut polymeric stent made from a material including poly (L-lactide).

17. A method for making a medical device, comprising:
providing a balloon having a shape memory forming prearranged pleats or wings, wherein the prearranged pleats or wings have kinks;
working-out the shape memory by increasing a pressure until the balloon is inflated, wherein when the balloon is inflated all of the kinks are substantially removed, followed by placing the balloon in a relaxed state wherein at least one of the prearranged pleats or wings is replaced by random folds; and
crimping the stent including plastically deforming the stent onto the balloon while the balloon has the relaxed state.

* * * * *